United States Patent [19]

Bredeweg

[11] 3,940,449
[45] Feb. 24, 1976

[54] β,β-CHLORINATED AND BROMINATED ETHERS

[75] Inventor: Corwin J. Bredeweg, Midland, Mich.

[73] Assignee: The Dow Chemical Company, Midland, Mich.

[22] Filed: Nov. 15, 1972

[21] Appl. No.: 306,916

[52] U.S. Cl...... 260/611 B; 260/611 A; 260/614 A; 260/614 R
[51] Int. Cl.² .................. C07C 43/18 ; C07C/43/28
[58] Field of Search........ 260/614 A, 614 R, 611 A, 260/611 B

[56] References Cited
UNITED STATES PATENTS

| | | | |
|---|---|---|---|
| 2,042,862 | 6/1936 | Perkins | 260/614 A X |
| 2,620,359 | 12/1952 | Britton et al. | 260/611 A |
| R22,217 | 11/1942 | Perkins | 260/614 R |

OTHER PUBLICATIONS
Bakker, et al, J. Am. Oil Chem. Soc., Vol. 44, pp. 517–521 (1967).
Shell, "Chem. Abst.", Vol. 68, Abstract No. 77734d (1968).

*Primary Examiner*—Donald G. Daus
*Assistant Examiner*—D. B. Springer
*Attorney, Agent, or Firm*—David H. Fifield

[57] ABSTRACT

Compounds are prepared having the formula

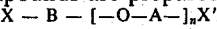

$$X - B - [-O-A-]_n X'$$

(hereinafter referred to as AAE's), wherein X and X' are chlorine or bromine atoms, $n$ is an integer from 1 to about 4, A is a vicinal alkylene group of up to about 8 carbon atoms and may bear a phenyl, chlorine, bromine or hydroxy substituent, and B is a vicinal alkylene group of from 8 to about 18 carbon atoms and may bear a chlorine, bromine or aromatic substituent.

The above compounds are prepared by reacting the halogen XX' with a mixture of the B mono-olefin (hereinafter BMO) and the epoxide AO. The compounds are useful as solvents and dielectric fluids.

12 Claims, No Drawings

β,β-CHLORINATED AND BROMINATED ETHERS

BACKGROUND OF THE INVENTION

1. Field of the Invention

The compounds claimed belong to the subclass of chlorinated and brominated alkyl- or aryl-substituted acyclic ethers in the field of organic chemistry. The process for making these compounds may be generally described as the addition to an olefinic material, of a chlorine or a bromine atom and an ether linkage, at a point of unsaturation in the olefinic material.

2. Description of the Prior Art:

The prior art teaches the preparation of ethers by the reaction of chlorine, ethylene oxide or propylene oxide and olefins: Trofimov, N. N., et al., USSR Pat. No. 179,765 (1966) (C.A. 65:p. 7101 (1966)); Perkins, G. A., Fr. Pat. No. 773,140 (1934); U.S. Pat. No. 2,042,862 (1936); Re. 22,217 (1942). Bromine has been substituted for chlorine in the above-mentioned process: Nesmeyanov, A. N., et al., *Izvest. Akad. Nauk. S.S.S.R., Otdel. Khim. Nauk.*, p. 708 (1951) (C.A. 46:p. 7514 (1952); and α,α'-dichlorinated ethers have been produced in manners unlike the one mentioned above: Toussaint, W. J., et al., U.S. Pat. No. 2,383,091 (1945); Nutting, H. S., et al., U.S. Pat. No. 2,095,612 (1937).

SUMMARY OF THE INVENTION

The invention consists of compounds having the formula

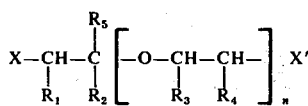

(AAE's), wherein X and X' are chlorine or bromine; $n$ is an integer from 1 to about 4; one of $R_1$ and $R_2$ is hydrogen or a hydrocarbon group and the other is a hydrocarbon group, provided that the sum of the carbon atoms in $R_1$ and $R_2$ is from 6 to about 16; one of $R_3$ and $R_4$ is hydrogen or methyl and the other is hydrogen, phenyl or an alkyl group of from 1 to about 7 carbon atoms which alkyl may bear a hydroxy, chlorine or bromine substituent; and $R_5$ is hydrogen or a methyl group which may be chlorinated or brominated. The compounds are useful as solvents and as dielectric fluids.

DETAILED DESCRIPTION OF THE INVENTION

The AAE compounds are prepared by mixing an excess amount of an AO, preferably ethylene oxide, propylene oxide, butylene oxide, styrene oxide, epichlorohydrin or glycidol, with a BMO of from 8 to about 18 carbon atoms, preferably a linear 1-olefin of 10–16 carbon atoms, suitably in the molar ratio of AO to BMO of about 2 to 1 and reacting the mixture by contacting with a sufficient amount of chlorine, bromine or bromine chloride, suitably with the halogen XX' and BMO in equimolar ratios.

The BMO employed may be substantially any aliphatic mono-olefin of from 8 to about 18 carbon atoms or a vinyl aromatic of from 8 to about 18 carbon atoms. Preferably the BMO has about 10 to 16 carbon atoms.

The preparation of the AAE compounds is conveniently carried out at atmospheric pressure and at a temperature of about 0° to 100°C. The temperature may be lowered as long as the reactants do not solidify. The temperature may be increased to at least about 200°C. if the operation is carried out in an enclosed pressurized vessel at a sufficient pressure to keep the nonhalogen reactants from boiling. The reaction with chlorine, bromine or bromine chloride is instantaneous. (Caution: The halogen should preferably be added to a mixture of the other two reactants since a reaction of the halogen with the epoxide alone may be quite violent.)

The reaction mixture is subsequently distilled, suitably at reduced pressures, to remove excess epoxide and other low boiling volatiles.

The compounds of the invention are produced in the above-described process where the major product consists of compounds of the above formula where $n$ is 1 but is usually found mixed with small amounts of telomers, compounds of the above formulae where $n$ is an integer from 2 to about 4; predominantly $n$ is 2 and 3. Since all of the reaction products have similar structural features, the mixed product is useful in the same solvent and dielectric fluid application as the major product, thereby obviating the need for separation, which could suitably be performed by fractional distillation.

DESCRIPTION OF SPECIFIC EMBODIMENTS OF THE INVENTION

Each of the following examples of the invention where $n$ is 1 mixed with the respective telomers is prepared by carrying out the above-described process at about 0°–50°C., under atmospheric pressure and employing the corresponding AO, BMO, and XX' reactants. The halogen is added to the AO-BMO mixture until the mixture begins to turn slightly yellow in color.

The preferred molar ratio of 2 to 1, AO to BMO, is employed to avoid large amounts of undesired excessively chlorinated or brominated by-products. Distillation at reduced pressure is used to remove excess AO and lower boiling by-products.

EXAMPLE 1

To a stirred solution of 1020 g. (6 m.) of dodecene-1 and 696 g. (12 m.) of propylene oxide, 525 g. (7.4 m.) of chlorine (100 parts Cl$_2$ diluted with 25 parts air) was added through a sparger tube at a rate of about 100 g. of chlorine per hour. The reaction mixture was cooled with an ice bath. This mixture was then distilled at reduced pressure, removing excess propylene oxide and other low boiling volatiles. When the pot temperature reached 145°C. and the head temperature 102°C., at 1 mm. pressure, the pot residue was recovered yielding about 1834 g. of product. The liquid product was found to be useful as a dielectric fluid, having a dielectric constant of 5.2 and a boiling point estimated at 340°C.

The inventions prepared in this example were the isomers of the structures:

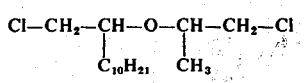

and

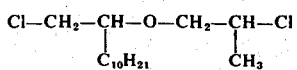

and higher telomers of these isomers.

EXAMPLE 2

A chlorine-air mixture containing 313 g. (4.4 m.) of chlorine was added to a solution of 416 g. (4 m.) of styrene and 464 g. (8 m.) of propylene oxide in the manner described in Example 1 in an ice bath, maintaining a reaction temperature of about 20°C. About 1000 g. of product, a liquid with a boiling point of 269°C. and a viscosity of 16.40 cps. at 25°C., was recovered by distillation under 0.4 mm. pressure with pot and head temperatures of 115°C. and 71°C. respectively. Vapor phase chromatography showed the product to be a mixture of lower telomers in the ratio of 15:6.5:1 where $n=1$, $n=2$ and $n$ 3, respectively.

Nuclear magnetic resonance spectroscopy revealed the presence of two isomers, in approximately a 1 to 1 ratio, for the $n=1$ telomer. These isomers were of the structures:

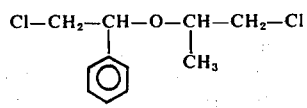

and

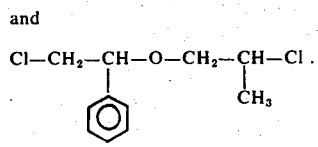

EXAMPLE 3

Para-tert.-butyl styrene, 960 g. (6 m.), was mixed with 696 g. (12 m.) of propylene oxide and reacted in an ice bath with 461 g. (6.5 m.) of chlorine in a chlorine-air mixture as described in Examples 1 and 2, above. About 1703 g. of product was recovered by distillation under 4 mm. pressure at a pot temperature of 104°C. and a head temperature of 31°C.

The inventions prepared in this example were the isomers of the structures:

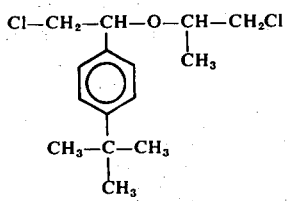

and

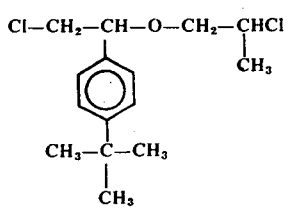

and higher telomers of these isomers.

In addition to the above-described specific embodiments of the invention, other mono-olefins and epoxides may be combined and reacted with the XX' halogen as described above. Some examples of other suitable reactant combinations which may be used to produce compounds of the invention are listed in the following table.

TABLE OF EXAMPLES OF THE
INVENTION - PRODUCTS OF THE FOLLOWING REACTANTS

| Monolefin (BMO) | Epoxide (AO) | Halogen (XX') |
|---|---|---|
| 4-Ethyloctene-1 | Ethylene oxide | $Cl_2$ |
| Octene-1 | Styrene oxide | $Br_2$ |
| Dodecene-1 | Glycidol | $Cl_2$ |
| Styrene | Epibromohydrin | $Cl_2$ |
| p.-tert.-Butylstyrene | Butylene oxide | $Br_2$ |
| Dodecene-2 | Epichlorohydrin | $Cl_2$ |
| 2-Vinylnaphthalene | Ethylene oxide | BrCl |
| p.-Vinyltoluene | Propylene oxide | $Cl_2$ |
| Decene-1 | 1,2-Octene oxide | $Br_2$ |
| 2-Bromomethyloctene-1 | Propylene oxide | BrCl |

The above products are high-boiling liquids useful as dielectric fluids and solvents.

I claim:

1. A compound

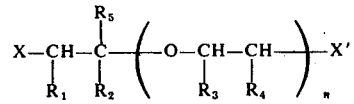

wherein X and X' are independently chlorine or bromine, $n$ is an integer from 1 to 4, one of $R_1$ and $R_2$ is hydrogen or a hydrocarbon group and the other is a hydrocarbon group, said hydrocarbon group being the residue of a $C_8$–$C_{18}$ monoolefin or of a $C_8$–$C_{16}$ vinyl aromatic, provided that the sum of the carbon atoms in $R_1$ and $R_2$ is from 6 to 16, one of $R_3$ and $R_4$ is hydrogen or methyl and the other is hydrogen, phenyl or an alkyl, monohydroxyalkyl, monochloroalkyl or monobromoalkyl group of from 1 to about 7 carbon atoms and $R_5$ is hydrogen, methyl, chloromethyl or bromomethyl.

2. A compound of claim 1 wherein $R_1$ is hydrogen and $R_2$ is a hydrocarbon group of from 6 to 16 carbon atoms.

3. A compound of claim 2 wherein $R_2$ is an aliphatic hydrocarbon of from 8 to 14 carbon atoms.

4. A compound of claim 3 wherein $R_2$ is a linear octyl or decyl group and $R_5$ is hydrogen.

5. A compound of claim 2 wherein $R_2$ is an aromatic hydrocarbon of from 6 to 16 carbon atoms.

6. A compound of claim 5 wherein $R_2$ is a phenyl, p.-tolyl, p.-tert.-butylphenyl or 2-naphthyl group and $R_5$ is hydrogen.

7. A compound of claim 1 wherein one of $R_3$ and $R_4$ is a methyl, chloromethyl, bromomethyl, hydroxymethyl, ethyl or phenyl group and the other is hydrogen.

8. A compound of claim 7 wherein $R_2$ is a linear octyl or decyl group, $R_5$ is hydrogen and $n$ is 1.

9. A compound of claim 8 wherein one of $R_3$ and $R_4$ is a methyl group and the other is hydrogen.

10. A compound of claim 1 wherein $n$ is 1.

11. A compound of claim 3 wherein one of $R_3$ and $R_4$ is hydrogen and the other is hydrogen or an alkyl group of from 1 to about 7 carbon atoms and $R_5$ is hydrogen.

12. A compound of claim 11 wherein $n$ is 1 and X and X' are both chlorine.

* * * * *

UNITED STATES PATENT AND TRADEMARK OFFICE
CERTIFICATE OF CORRECTION

PATENT NO. : 3,940,449
DATED : February 24, 1976
INVENTOR(S) : Corwin J. Bredeweg It is certified that error appears in the above-identified patent and that said Letters Patent are hereby corrected as shown below:

Title Page, under "Other Publications", the Shell reference insert after "(1968)" --of Neth. appln. No. 6,607,907--;

Column 1, line 24, "$\alpha,\alpha'$-" should read --$\beta,\beta'$- --;

Column 2, line 18, "formulae" should read --formula--;

Column 3, line 15, between "n" and "3" insert -- $\geq$ --.

Signed and Sealed this

Thirty-first Day of August 1976

[SEAL]

Attest:

RUTH C. MASON
Attesting Officer

C. MARSHALL DANN
Commissioner of Patents and Trademarks